(12) United States Patent
Goonewardena et al.

(10) Patent No.: US 9,931,412 B2
(45) Date of Patent: Apr. 3, 2018

(54) TARGETED THERANOSTICS

(71) Applicant: THE REGENTS OF THE UNIVERSITY OF MICHIGAN, Ann Arbor, MI (US)

(72) Inventors: Sascha N. Goonewardena, Ann Arbor, MI (US); Bertram Pitt, Ann Arbor, MI (US); Hong Zong, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 14/175,733

(22) Filed: Feb. 7, 2014

(65) Prior Publication Data
US 2014/0227297 A1 Aug. 14, 2014

Related U.S. Application Data

(60) Provisional application No. 61/762,661, filed on Feb. 8, 2013.

(51) Int. Cl.
| | | |
|---|---|---|
| *A61K 47/48* | (2006.01) | |
| *A61K 49/00* | (2006.01) | |
| *A61K 49/08* | (2006.01) | |
| *A61K 47/65* | (2017.01) | |
| *A61K 47/55* | (2017.01) | |
| *A61K 47/64* | (2017.01) | |
| *A61K 47/68* | (2017.01) | |

(52) U.S. Cl.
CPC ...... *A61K 47/48384* (2013.01); *A61K 47/551* (2017.08); *A61K 47/64* (2017.08); *A61K 47/644* (2017.08); *A61K 47/65* (2017.08); *A61K 47/6803* (2017.08); *A61K 49/0002* (2013.01); *A61K 49/0043* (2013.01); *A61K 49/0052* (2013.01); *A61K 49/085* (2013.01)

(58) Field of Classification Search
None
See application file for complete search history.

(56) References Cited

U.S. PATENT DOCUMENTS

| | | | |
|---|---|---|---|
| 3,927,193 | A | 12/1975 | Hansen et al. |
| 4,036,945 | A | 7/1977 | Haber |
| 4,331,647 | A | 5/1982 | Goldenberg |
| 4,348,376 | A | 9/1982 | Goldenberg |
| 4,361,544 | A | 11/1982 | Goldenberg |
| 4,444,744 | A | 4/1984 | Goldenberg |
| 4,460,459 | A | 7/1984 | Shaw et al. |
| 4,460,561 | A | 7/1984 | Goldenberg |
| 4,468,457 | A | 8/1984 | Goldenberg |
| 4,624,846 | A | 11/1986 | Goldenberg |
| 4,735,210 | A | 4/1988 | Goldenberg |
| 4,818,709 | A | 4/1989 | Primus et al. |
| 2005/0090732 | A1 | 4/2005 | Ivkov et al. |
| 2005/0266067 | A1* | 12/2005 | Sengupta ............... A61K 9/167 424/450 |
| 2007/0066580 | A1 | 3/2007 | Leonardi et al. |
| 2009/0264317 | A1 | 10/2009 | Ofir et al. |
| 2011/0085974 | A1* | 4/2011 | Chung ............. A61K 47/48069 424/1.65 |
| 2011/0123436 | A1 | 5/2011 | Chang et al. |
| 2012/0171227 | A1 | 7/2012 | Baker et al. |

FOREIGN PATENT DOCUMENTS

| | | |
|---|---|---|
| WO | 2012/135592 A2 | 10/2012 |
| WO | WO 2012135592 A2 * | 10/2012 ....... A61K 47/48138 |

OTHER PUBLICATIONS

Katritzky & Rees (eds.), Comprehensive Heterocyclic Chemistry, vol. 1-9, Pergamon Oxford 1984.
Katritzky et al. (eds.), Comprehensive Heterocyclic Chemistry II, vol. 1-11, Pergamon, Oxford 1996.
Auzzas et al., "Targeting alphavbeta3 integrin: design and applications of mono- and multifunctional RGD-based peptides and semipeptides." Curr Med Chem. 2010; 17(13):1255-99.
Beer et a., "PET Imaging of Integrin αVβ3 Expression." Theranostics. Jan. 17, 2011; 1:48-57.
Beer et al., "PET imaging of αvβ3 expression in cancer patients." Methods Mol Biol. 2011; 680:183-200.
Cortinovis et al., "Aldosterone and progression of kidney disease." Ther Adv Cardiovasc Dis. Apr. 2009; 3(2):133-43.
Daniels et al., "The transferrin receptor part I: Biology and targeting with cytotoxic antibodies for the treatment of cancer." Clin Immunol. Nov. 2006; 121(2):144-58.
Derbre et al., "Annonaceous Acetogenins: The Hydroxyl Groups and THF Rings are Crucial Structural Elements for Targeting the Mitochondria, Demonstration with the Systhesis of Fluorescent Squamocin Analogues." Chem Bio Chem 2005, 6(6): 979-982.
Dietz et al., "A number of marketed dihydropyridine calcium channel blockers have mineralocorticoid receptor antagonist activity." Hypertension. Mar. 2008; 51(3):742-8.
Fieser and Fieser's Reagents for Organic Synthesis, Wiley & Sons: New York, vols. 1-21.
Igarashi et al., "PMAP: databases for analyzing proteolytic events and pathways." Nucleic Acids Res. Jan. 2009; 37 (Database issue): D611-8.
Jung et al., "Theranostic systems assembled in situ on demand by host-guest chemistry." Biomaterials 2011, 32:7687-7694.
Kim et al., "A WKYMVm-Containing Combination Elicits Potent Anti-Tumor Activity in Heterotopic Cancer Animal Model." PLoS One Jan. 2012, 7(1):e30522.
Krauss et al., "Emerging antibody-based HER2 (ErbB-2/neu) therapeutics." Breast Dis. 2000; 11:113-24.
Lange et al., "TopFIND 2.0—linking protein termini with proteolytic processing and modifications altering protein function." Nucleic Acids Res. Jan. 2012; 40(D1): D351-D361.
(Continued)

*Primary Examiner* — Misook Yu
*Assistant Examiner* — Kauser M Akhoon
(74) *Attorney, Agent, or Firm* — Casimir Jones, S.C.

(57) ABSTRACT

Provided herein is technology relating to theranostic agents and particularly, but not exclusively, to compositions comprising cell-specific theranostic agents and associated methods and systems for using the cell-specific theranostic agents to treat subjects.

6 Claims, 1 Drawing Sheet

(56) References Cited

OTHER PUBLICATIONS

Larock, "Comprehensive Organic Transformations: A Guide to Functional Group Preparations" 2nd ed. Wiley-VCH New York Nov. 1999.
Ma et al., "Structure-transfection activity relationships with glucocorticoid-polyethyl-enimine conjugate nuclear gene delivery systems." Biomaterials 2009, 30:3780-3789.
Morrison et al., "Integrin imaging to evaluate treatment response." Theranostics. Feb. 11, 2011; 1:149-53.
Nam et al., "Primary cardiomyocyte-targeted bioreducible polymer for efficient gene delivery to the myocardium." Biomaterials. Nov. 2010; 31(31):8081-7.
Paquette, "Organic Reactions" Wiley & Sons: New York, vols. 1-40, Jul. 1991.
Qian et al., "Targeted drug delivery via the transferrin receptor-mediated endocytosis pathway." Pharmacol Rev. Dec. 2002; 54(4):561-87.
Remington's Pharmaceutical Sciences, 17th edition, p. 1418 (1985).
Remington's Pharmaceutical Sciences, 18th edition, (1990), ed. A.R. Gennaro, Mack Publishing Co.
Santra et al., "Cell-Specific, Activatable and Theranostic Prodrug for Dual Targeted Cancer Imaging and Therapy." J. Am. Chem. Soc. Oct. 19, 2011, 133(41): 16680-16688.
Sawhney et al., "Bioerodible hydrogels based on photopolymerized poly(ethylene glycol)-co-poly(alpha-hydroxy acid) diacrylate macromers" Macromolecules 1993, 26 (4):581-587.
Sudimack et al., "Targeted drug delivery via the folate receptor." Adv Drug Deliv Rev. Mar. 30, 2000; 41(2):147-62.
Syngle et al., "Effect of spironolactone on endothelial dysfunction in rheumatoid arthritis." Scand J Rheumatol. Jan.-Feb. 2009; 38(1):15-22.
Taheri S et. al., "Spironolactone in chronic hemodialysis patients improves cardiac function." Saudi J Kidney Dis Transpl. May 2009; 20(3):392-7.
Takai et al., "Eplerenone inhibits atherosclerosis in nonhuman primates." Hypertension. Nov. 2005; 46(5):1135-9.
Thomas et al., "Folate-Targeted Nanoparticles Show Efficacy in the Treatment of Inflammatory arthritis." Arthritis & Rheumatism Sep. 2011, 63(9): 2671-2680.
Trost & Fleming (eds.), "Comprehensive Organic Synthesis" vol. 1-9 Pergamon, Oxford 1991.
Waldmann, "Immunotherapy: past, present and future." Nat Med. Mar. 2003; 9(3):269-77.
Zhou et al., "Radiolabeled Cyclic RGD Peptides as Radiotracers for Imaging Tumors and Thrombosis by SPECT." Theranostics. Jan. 18, 2011; 1:58-82.

* cited by examiner

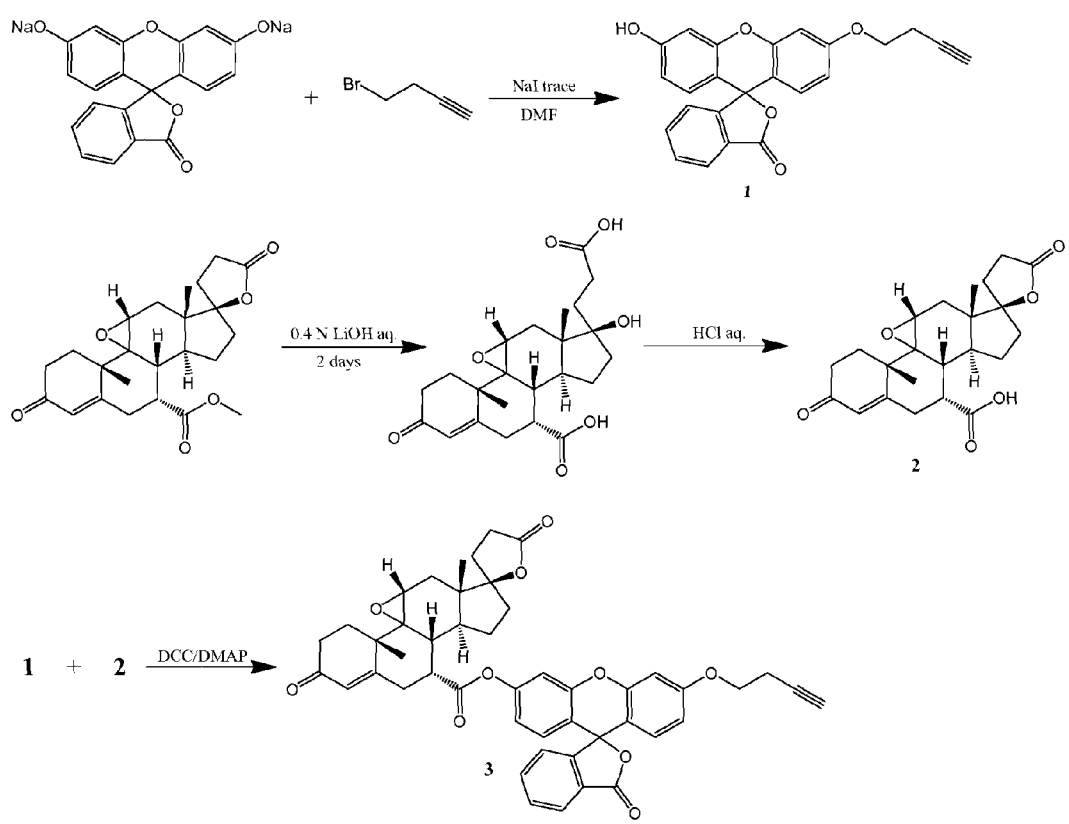

TARGETED THERANOSTICS

This application claims priority to U.S. provisional patent application 61/762,661, filed Feb. 8, 2013, which is incorporated herein by reference in its entirety.

FIELD OF TECHNOLOGY

Provided herein is technology relating to theranostic agents and particularly, but not exclusively, to compositions comprising cell-specific theranostic agents and associated methods and systems for using the cell-specific theranostic agents to treat subjects.

BACKGROUND

Many diseases are caused by cell-specific (e.g., tissue specific, organ specific, etc.) problems in the patient. Oftentimes, drugs and other treatment agents that act to counter diseases in these cells, tissues, and organs that are associated with the disease also cause unwanted side effects due to their actions in other cell and tissue types or due to general systemic activity in the patient.

For instance, aldosterone is a mineralocorticoid receptor agonist that promotes inflammation and cardiovascular disease. Mineralocorticoid receptor antagonists provide one of the few therapeutic approaches to treat heart failure and reduced left ventricular ejection fraction. The mineralocorticoid receptor antagonists spironolactone and eplerenone inhibit the mineralocorticoid receptor driven inflammatory modules and are effective in inhibiting sodium reabsorption and decreasing blood pressure in the cardiovascular system, thus aiding the treatment of cardiovascular disease. However, despite these clinical benefits on the heart and blood vessels, traditional mineralocorticoid receptor antagonists also produce unwanted side effects such as gynecomastia and mastodynia in men due to off-target effects on steroid receptors and hyperkalemia due to off-target actions in the kidney. As another example, conventional chemotherapies (e.g., for cancer) are administered systemically. While killing of only the cancer cells (e.g., of a tumor) is desirable, systemic administration exposes healthy, non-cancerous cells to these powerful and toxic chemotherapeutic agents, often producing sickness and other symptoms such as hair loss.

Thus, there is a need for agents that direct small molecules (e.g., drugs and other therapeutic agents) to specific cells, tissues, or organs for treatment, thereby minimizing or preventing the delivery of these small molecules to other cells, tissues, and organs and, consequently, reduces or eliminates off-target and generalized side effects.

SUMMARY

The present technology is related to methods, compositions, and systems for delivering small molecules to targeted areas of a subject's body such as particular organs, tissues, cells, etc., and not to non-targeted areas of a subject's body. In addition, the technology provides for monitoring delivery of the small molecules to the targeted areas of a subject's body as a measure of therapeutic efficacy of the small molecules.

In some aspects, particular synthetic approaches provide embodiments of compounds that comprise several components: a drug, a targeting group, a linker moiety, a quantifiable detectable moiety (e.g., a fluorescent reporter), and/or other functional groups. The targeting group targets the compounds for uptake by particular classes or types of cells, e.g., by receptors that specifically recognize the targeting group. The drug component and the quantifiable detectable moiety are connected by the linker and are inactive when connected by the linker in the compound. When the linker is broken (e.g., by activities such as esterases or other enzymes associated with the particular targeted classes or types of cells), the drug and the quantifiable fluorescent reporter are released, whereupon the drug becomes active and the quantifiable detectable moiety becomes detectable (e.g., a fluorescent dye that emits detectable energy when released from the linker). As such, the cell-specific targeting and cell-specific processing to release the drug and detectable moiety provide a functionality to monitor delivery of the drug to the target cells and, as such, aid in assessing its therapeutic efficacy. By combining the diagnostic reporter with the therapeutic effects of these compounds, it is contemplated that the technology allows the amount of small molecule delivered to the target site to be based on the requirements of individual patients. Using this theranostic approach, several exemplary compounds are provided based on the general scaffold of drug, linker, reporter, targeting group, and/or other functional group. These agents provide specific therapeutic benefits without the systemic toxicities that are associated with the conventional approaches. This new class of compounds finds use in the diagnosis and therapy of a broad spectrum of diseases.

Accordingly, provided herein are embodiments of theranostic compounds comprising two or more of a bioactive component, a detectable component, a targeting component, and a linker. In some embodiments, the linker links the bioactive component and the detectable component. In some embodiments, the bioactive component is a drug. In some embodiments, the detectable component is a fluorogenic dye (e.g., fluorescein), an imaging agent, or a contrast agent (e.g., 1,4,7,10-tetraazacyclododecane-1,4,7,10-tetraacetic acid) complexed with gadolinium). In some embodiments, the linker is an ester or a protease-specific peptide. In some embodiments, the targeting component is a peptide having the sequence RGD or CWLSEAGPVVTVRALRGTGSW. In some embodiments the targeting component is folic acid or mannose. In some embodiments, the bioactive component is a mineralocorticoid receptor antagonist, a histone deacetylase inhibitor, or a chemotherapeutic. Exemplary embodiments include a theranostic compound wherein the bioactive component is eplerenone, suberoylanilide hydroxamic acid, or methotrexate, e.g., a theranostic compound having a structure according to

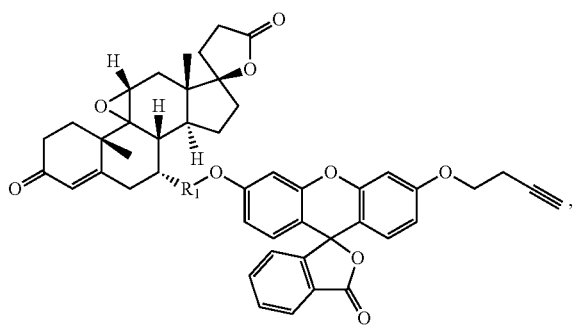

wherein $R_1$ is the linker. In some embodiments the theranostic compound further comprises a functional group such as a polymer, a dendrimer, a magnetic bead, or a polymer bead.

Also provided are embodiments of methods for treating a subject, wherein the methods comprise administering a compound comprising a bioactive component linked to a detectable component and measuring a level of the detectable component in a sample from the subject. In some embodiments, the methods further comprise a second administering of the compound based on the level of the detectable component in the sample from the subject. In some embodiments, the methods further comprise determining an amount of the bioactive component at a target site of the subject. In some embodiments, the compound further comprises a targeting component and in some embodiments the compound further comprises a linker linking the bioactive component to the detectable component. In some embodiments, the methods further comprise breaking the linker. In some embodiments breaking the linker occurs at a target site of the subject, e.g., by a cell-specific activity at the target site (e.g., an esterase or protease). Embodiments are provided in which an embodiment of the compounds disclosed is administered to a subject. Embodiments are also provided for use of the compounds described for delivering an appropriate dose of a bioactive component to a subject. In addition to therapeutic uses, the compounds find use in diagnostic, screening, and research applications.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings:

FIG. 1 shows a scheme for the synthesis of eplerenone-7'-fluorescein-alkyne.

DETAILED DESCRIPTION

Provided herein is technology relating to therapeutic and diagnostic agents and particularly, but not exclusively, to compositions comprising cell-specific therapeutic and diagnostic agents and associated methods and systems for using the cell-specific therapeutic and diagnostic agents to treat subjects.

The section headings used herein are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the technology may be readily combined, without departing from the scope or spirit of the technology.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein a "target site" is a site of a subject at which it is desired for a bioactive agent to be delivered and to be active. A target site may be a cell, a cell type, a tissue, an organ, an area, or other designation of a subject's anatomy and/or physiology.

The terms "protein" and "polypeptide" refer to compounds comprising amino acids joined via peptide bonds and are used interchangeably. Conventional one and three-letter amino acid codes are used herein as follows—Alanine: Ala, A; Arginine: Arg, R; Asparagine: Asn, N; Aspartate: Asp, D; Cysteine: Cys, C; Glutamate: Glu, E; Glutamine: Gln, Q; Glycine: Gly, G; Histidine: His, H; Isoleucine: Ile, I; Leucine: Leu, L; Lysine: Lys, K; Methionine: Met, M; Phenylalanine: Phe, F; Proline: Pro, P; Serine: Ser, S; Threonine: Thr, T; Tryptophan: Trp, W; Tyrosine: Tyr, Y; Valine: Val, V. As used herein, the codes Xaa and X refer to any amino acid.

In some embodiments compounds of the technology comprise an antibody component or moiety, e.g., an antibody or fragments or derivatives thereof. As used herein, an "antibody", also known as an "immunoglobulin" (e.g., IgG, IgM, IgA, IgD, IgE), comprises two heavy chains linked to each other by disulfide bonds and two light chains, each of which is linked to a heavy chain by a disulfide bond. The specificity of an antibody resides in the structural complementarity between the antigen combining site of the antibody (or paratope) and the antigen determinant (or epitope). Antigen combining sites are made up of residues that are primarily from the hypervariable or complementarity determining regions (CDRs). Occasionally, residues from non-hypervariable or framework regions influence the overall domain structure and hence the combining site. In some embodiments the targeting moiety is a fragment of antibody, e.g., any protein or polypeptide-containing molecule that comprises at least a portion of an immunoglobulin molecule such as to permit specific interaction between said molecule and an antigen. The portion of an immunoglobulin molecule may include, but is not limited to, at least one complementarity determining region (CDR) of a heavy or light chain or a ligand binding portion thereof, a heavy chain or light chain variable region, a heavy chain or light chain constant region, a framework region, or any portion thereof. Such fragments may be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. The various portions of antibodies can be joined together chemically by conventional techniques, or can be prepared as a contiguous protein using genetic engineering techniques.

Fragments of antibodies include, but are not limited to, Fab (e.g., by papain digestion), F(ab')$_2$ (e.g., by pepsin digestion), Fab' (e.g., by pepsin digestion and partial reduction) and Fv or scFv (e.g., by molecular biology techniques) fragments.

A Fab fragment can be obtained by treating an antibody with the protease papaine. Also, the Fab may be produced by inserting DNA encoding a Fab of the antibody into a vector for prokaryotic expression system or for eukaryotic expression system, and introducing the vector into a prokaryote or eukaryote to express the Fab. A F(ab')$_2$ may be obtained by treating an antibody with the protease pepsin. Also, the F(ab')$_2$ can be produced by binding a Fab' via a thioether bond or a disulfide bond. A Fab may be obtained by treating F(ab')$_2$ with a reducing agent, e.g., dithiothreitol. Also, a Fab' can be produced by inserting DNA encoding a Fab' fragment of the antibody into an expression vector for a prokaryote or an expression vector for a eukaryote, and introducing the vector into a prokaryote or eukaryote for its expression. A Fv fragment may be produced by restricted cleavage by pepsin, e.g., at 4° C. and pH 4.0. (a method called "cold pepsin digestion"). The Fv fragment consists of the heavy chain variable domain ($V_H$) and the light chain variable domain ($V_L$) held together by strong noncovalent interaction. A scFv fragment may be produced by obtaining cDNA encoding the $V_H$ and $V_L$ domains as previously described, constructing DNA encoding scFv, inserting the DNA into an expression vector for prokaryote or an expression vector for eukaryote, and then introducing the expression vector into a prokaryote or eukaryote to express the scFv.

In general, antibodies can usually be raised to any antigen, using the many conventional techniques now well known in the art. Any targeting antibody to an antigen which is found in sufficient concentration at a site in the body of a mammal which is of diagnostic or therapeutic interest can be used to make the compounds provided herein.

As used herein, the term "conjugated" refers to when one molecule or agent is physically or chemically coupled or adhered to another molecule or agent. Examples of conjugation include covalent linkage and electrostatic complexation. The terms "complexed," "complexed with," and "conjugated" are used interchangeably herein.

As used herein, the term "treatment" is defined as the application or administration of a therapeutic agent described herein, or identified by a method described herein, to a patient, or application or administration of the therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease, or the predisposition toward disease.

The term "alkyl" shall mean straight or branched chain alkanes of one to ten total carbon atoms, or any number within this range (i.e., methyl, ethyl, 1-propyl, 2-propyl, n-butyl, s-butyl, t-butyl, etc.).

The term "aryl" as used herein, except where otherwise specifically defined, refers to unsubstituted, mono- or poly-substituted aromatic groups such as phenyl or naphthyl.

Unless otherwise specifically noted as only "unsubstituted" or only "substituted", defined groups are unsubstituted or substituted. Preferably, substituents are selected from the group that includes, but is not limited to, halo, $C_1$-$C_{20}$ alkyl, $CF_3$, $NH_2$, $N(C_1$-$C_6$ alkyl)$_2$, $NO_2$, oxo, CN, $N_3$, OH, $O(C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl)S(O)$_{0-2}$, aryl-S(O)$_{0-2}$, ($C_0$-$C_6$ alkyl)S(O)$_{0-2}$($C_0$-$C_6$ alkyl), ($C_0$-$C_6$ alkyl)C(O)NH, $H_2$N—C(NH), $O(C_1$-$C_6$ alkyl)$CF_3$, ($C_0$-$C_6$ alkyl)C(O), ($C_0$-$C_6$ alkyl)OC(O), ($C_0$-$C_6$ alkyl)O($C_1$-$C_6$ alkyl), ($C_0$-$C_6$ alkyl)C(O)$_{1-2}$ ($C_0$-$C_6$ alkyl), ($C_0$-$C_6$ alkyl)OC(O)NH, aryl, aralkyl, heteroaryl, heterocyclylalkyl, halo-aryl, halo-aralkyl, halo-heterocycle, halo-heterocyclylalkyl, cyano-aryl, cyano-aralkyl, cyano-heterocycle, and cyano-heterocyclylalkyl. The term "substituted" is understood to include mono- and poly-substitution by a named substituent to the extent such single and multiple substitution (including multiple substitution at the same site) is chemically allowed. Unless expressly stated to the contrary, substitution by a named substituent is permitted on any atom in a ring (e.g., aryl, a heteroaromatic ring, or a saturated heterocyclic ring) provided such ring substitution is chemically allowed and results in a stable compound.

A "stable" compound is a compound that can be prepared and isolated and whose structure and properties remain or can be caused to remain essentially unchanged for a period of time sufficient to allow use of the compound for the purposes described herein (e.g., therapeutic, prophylactic, and/or diagnostic administration to a subject).

As a result of the selection of substituents and substituent patterns, certain of the compounds of the present technology can have asymmetric centers and can occur as mixtures of stereoisomers, or as individual diastereomers, or enantiomers. All isomeric forms of these compounds, whether isolated or in mixtures, are within the scope of the present technology. Pharmaceutically acceptable salts include both the metallic (inorganic) salts and organic salts, a list of which is given in Remington's Pharmaceutical Sciences, 17th Edition, pg. 1418 (1985). It is well known to one skilled in the art that an appropriate salt form is chosen based on physical and chemical properties. As will be understood by those skilled in the art, pharmaceutically acceptable salts include, but are not limited to salts of inorganic acids such as hydrochloride, sulfate, phosphate, diphosphate, hydrobromide, and nitrate; or salts of an organic acid such as malate, maleate, fumarate, tartrate, succinate, citrate, acetate, lactate, methanesulfonate, p-toluenesulfonate or palmoate, salicylate, and stearate. Similarly pharmaceutically acceptable cations include, but are not limited to sodium, potassium, calcium, aluminum, lithium, and ammonium (especially ammonium salts with secondary amines). Also included within the scope of this technology are crystal forms, hydrates, and solvates.

Compositions according to the technology can be administered in the form of pharmaceutically acceptable salts. The term "pharmaceutically acceptable salt" refers to a salt that possesses the effectiveness of the parent compound and is not biologically or otherwise undesirable (e.g., is neither toxic nor otherwise deleterious to the recipient thereof). Suitable salts include acid addition salts that may, for example, be formed by mixing a solution of the compound of the present technology with a solution of a pharmaceutically acceptable acid such as hydrochloric acid, sulfuric acid, acetic acid, trifluoroacetic acid, or benzoic acid. Certain of the compounds employed in the present technology may carry an acidic moiety (e.g., COOH or a phenolic group), in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (COOH) or alcohol group being present, pharmaceutically acceptable esters can be employed to modify the solubility or hydrolysis characteristics of the compound.

The term "administration" and variants thereof (e.g., "administering" a compound) in reference to a compound mean providing the compound or a prodrug of the compound to the individual in need of treatment or prophylaxis. When a compound of the technology or a prodrug thereof is provided in combination with one or more other active agents, "administration" and its variants are each understood to include provision of the compound or prodrug and other agents at the same time or at different times. When the agents of a combination are administered at the same time, they can be administered together in a single composition or they can be administered separately. As used herein, the term "composition" is intended to encompass a product comprising the specified ingredients in the specified amounts, as well as any product that results, directly or indirectly, from combining the specified ingredients in the specified amounts.

By "pharmaceutically acceptable" is meant that the ingredients of the pharmaceutical composition must be compatible with each other and not deleterious to the recipient thereof.

The term "subject" as used herein refers to an animal, preferably a mammal, most preferably a human, who has been the object of treatment, observation, or experiment.

The term "effective amount" as used herein means that amount of active compound or pharmaceutical agent that elicits the biological or medicinal response in a cell, tissue, organ, system, animal, or human that is being sought by a researcher, veterinarian, medical doctor, or other clinician. In some embodiments, the effective amount is a "therapeutically effective amount" for the alleviation of the symptoms of the disease or condition being treated. In some embodiments, the effective amount is a "prophylactically effective amount" for prophylaxis of the symptoms of the disease or condition being prevented. The term also includes herein the amount of active compound sufficient to inhibit the mineralocorticoid receptor and thereby elicit a response being sought (e.g., an "inhibition effective amount"). When the active compound is administered as the salt, references to the amount of active ingredient are to the free form (the non-salt form) of the compound. In some embodiments, this amount is between 1 mg and 1000 mg per day, e.g., between 1 mg and 500 mg per day (between 1 mg and 200 mg per day).

In the method of the present technology, compounds, optionally in the form of a salt, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the technology can, for example, be administered orally, parenterally (including subcutaneous injections, intravenous, intramuscular, intrasternal injection, or infusion techniques), by inhalation spray, or rectally, in the form of a unit dosage of a pharmaceutical composition containing an effective amount of the compound and conventional non-toxic pharmaceutically-acceptable carriers, adjuvants, and vehicles. Liquid preparations suitable for oral administration (e.g., suspensions, syrups, elixirs, and the like) can be prepared according to techniques known in the art and can employ any of the usual media such as water, glycols, oils, alcohols, and the like. Solid preparations suitable for oral administration (e.g., powders, pills, capsules, and tablets) can be prepared according to techniques known in the art and can employ such solid excipients as starches, sugars, kaolin, lubricants, binders, disintegrating agents, and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution, or a solution containing a mixture of saline and glucose. Further description of methods suitable for use in preparing pharmaceutical compositions for use in the present technology and of ingredients suitable for use in said compositions is provided in *Remington's Pharmaceutical Sciences*, 18th edition, edited by A. R. Gennaro, Mack Publishing Co., 1990. Compounds of the present technology can be made by a variety of methods depicted in the synthetic reaction schemes provided herein. The starting materials and reagents used in preparing these compounds generally are either available from commercial suppliers, such as Aldrich Chemical Co., or are prepared by methods known to those skilled in the art following procedures set forth in references such as Fieser and Fieser's *Reagents for Organic Synthesis*, Wiley & Sons: New York, Volumes 1-21; R. C. LaRock, *Comprehensive Organic Transformations*, 2nd edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 1-40. The synthetic reaction schemes and examples provided herein are merely illustrative of some methods by which the compounds of the present technology can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Embodiments of the Technology

Provided herein is technology relating to theranostic agents and particularly, but not exclusively, to compositions comprising cell-specific theranostic agents and associated methods. According to at least some embodiments the present invention also relates to the use of markers and antibodies according to at least some embodiments of the technology for theranostics. The term theranostics describes the use of diagnostic testing to diagnose a disease, choose a treatment regime according to the results of diagnostic testing and/or monitor the patient response to therapy according to the results of diagnostic testing. Theranostic tests optionally may be used to select patients for treatments that are particularly likely to benefit them and unlikely to produce side-effects. They can also provide an early and objective indication of treatment efficacy in individual patients, so that (if necessary) the treatment can be altered with a minimum of delay. Thus, the field of theranostics represents the intersection of diagnostic testing information that predicts the response of a patient to a treatment with the selection of the appropriate treatment for that particular patient and systems for using the cell-specific theranostic agents to treat subjects. Although the disclosure herein refers to certain illustrated embodiments, it is to be understood that these embodiments are presented by way of example and not by way of limitation.

at the bottom right is a flourescein comprising a reactive alkyne at the right side for derivatization with a targeting moiety appropriate for the particular application in which this compound will find use. The technology is modular such that the components can be assembled to provide compounds with a range of drug activities targeted to a range of cells and, in some embodiments, providing a range of detectable moieties and/or other functionalities. For example, in another exemplary embodiment, a compound has the structure:

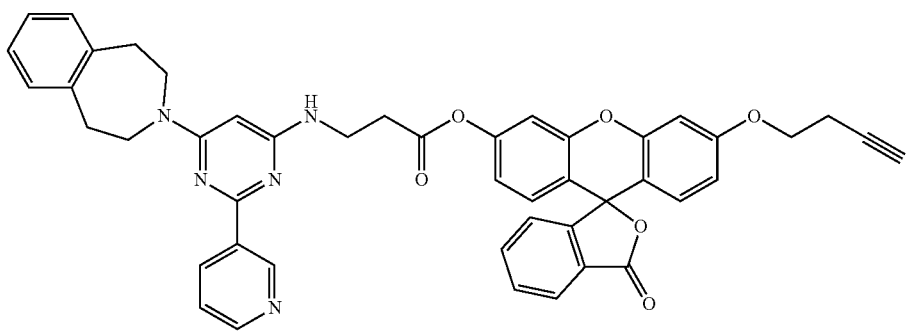

The compounds according to the technology comprise a drug, a linker, a detectable moiety (e.g., a fluorogenic dye), a targeting group, and/or one or more other functional groups. The compounds have the general structure:

D-L-F-T in which D is a drug, L is a linker, F is a detectable moiety, and T is a targeting group. The compounds may also comprise one or more other functional groups attached to any of these components. The linker links the drug and the detectable moiety; when linked by the linker, the drug is not active and the detectable moiety is not detectable (e.g., at the wavelength used to monitor emission of the fluorogenic dye). The targeting group targets the compound for a particular cell type (e.g., for uptake). When the compound reaches the target site, the linker is processed (e.g., by hydrolysis or other breaking of the linker) to release the drug in its active form and detectable moiety in its detectable form. As such, detection of the detectable moiety signifies delivery of the active drug at the target cell.

In one exemplary and specific embodiment, a compound has the structure

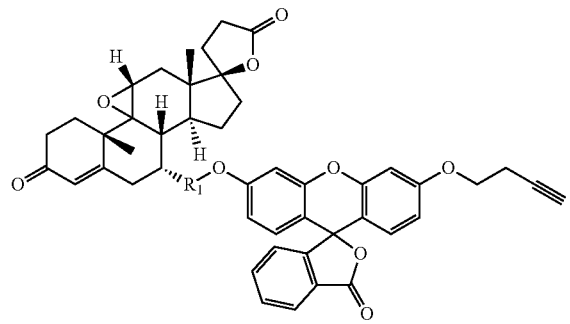

In this structure, the moiety at the top left is eplerenone, the linker $R_1$ is a group such as an ester linkage, and the moiety This exemplary compound (e.g., 3'-(but-3-yn-1-yloxy)-3-oxo-3H-spiro[isobenzofuran-1,9'-xanthen]-6'-yl 3-((6-(4,5-dihydro-1H-benzo[d]azepin-3(2H)-yl)-2-(pyridin-3-yl)pyrimidin-4-yl)amino)propanoate) comprises a drug moiety that is a histone demethylase inhibitor, a linker moiety that is an ester linker, a detectable moiety that is a fluorescein, and a reactive alkyne for derivatization with a targeting moiety.

Components of the Compounds

1. Drugs

The technology contemplates the use of any biologically active agent as the drug component. As used herein, a drug is a substance that may have medicinal, intoxicating, performance enhancing, or other effects when taken or put into an organism (e.g., a human body or the body of another animal), such as a chemical substance used in the treatment, cure, prevention, or diagnosis of disease or used otherwise to modulate (e.g., to enhance) physical or mental well-being. Such agents include, but are not limited to, a toxin, an enzyme, an antibody (or fragment or derivative of an antibody), an aptamer, an inhibitor, a small molecule, a metabolite, a cofactor, a vitamin, a hormone, a neurotransmitter, a stimulant, a modulator of neurotransmitters, (e.g., a cholinergic, a dopaminergic, a serotonergic), antagonists and agonists of biological targets, etc. The drug component may be a natural compound, an analog of a natural compound, or a synthetic compound. Particular exemplary embodiments of drugs are discussed below.

Mineralocorticoid Receptor Antagonists

In some embodiments, the drug is a mineralocorticoid receptor antagonist. The mineralocorticoid receptor (often referred to by the abbreviations MR, MLR, and MCR) is a nuclear receptor. It is often called the aldosterone receptor because a key activating ligand for this receptor is aldosterone. Nuclear receptors are a class of proteins found within the interior of cells. They have the ability to directly bind to DNA and regulate the expression of adjacent genes. The regulation of gene expression by a nuclear receptor occurs when a ligand is present and binds to the nuclear receptor.

Ligand binding results in a conformational change in the receptor that activates the receptor and brings about regulation of gene expression.

The mineralocorticoid receptor is expressed in many tissues, such as the kidney, colon, heart, central nervous system (hippocampus), brown adipose tissue, and sweat glands. In epithelial tissues, its activation leads to the expression of proteins regulating ionic and water transports (e.g., the epithelial sodium channel (ENaC), Na+/K+ pump, serum and glucocorticoid induced kinase or SGK1) resulting in the reabsoprtion of sodium, and as a consequence, an increase in extracellular volume, increase in blood pressure, and an excretion of potassium to maintain a normal salt concentration in the body.

The receptor is activated upon the binding of ligands known as mineralocorticoids. These include aldosterone and deoxycorticosterone as well as glucocorticoids such as cortisol and corticosterone. The mineralocorticoid receptor also responds to some progestins.

The mineralocorticoid receptor antagonists, also known as aldosterone antagonists, are a known class of drugs that antagonize the action of aldosterone at mineralocorticoid receptors. Antagonism of these receptors inhibits sodium resorption in the collecting duct of the nephron in the kidneys. This inhibits sodium/potassium exchange, thus reducing urinary potassium excretion and weakly increasing water excretion. This diuretic activity reduces edema and blood pressure. As a consequence, this group of drugs is often used for the treatment of primary hyperaldosteronism and edematous conditions including congestive heart failure, cirrhosis of the liver accompanied by edema and/or ascites, the nephrotic syndrome, essential hypertension, and hypokalemia. In addition, mineralocorticoid receptor antagonists have anti-inflammatory and anti-fibrotic effects that are independent of the blood pressure lowering effects. Treatments using mineralocorticoid receptor antagonists have provided beneficial effects in chronic kidney disease (Cortinovis et. al. (2009) *Ther Adv Cardiovasc Dis* 3: 133-43), end stage renal disease (Taheri et al. (2009) *Saudi J Kidney Dis Transspl* 79: 863-9), arthritis (Syngle et al. (2009) *Scand J Rheumatol* 38: 15-22), atherosclerosis (Takai et al. (2005) *Hypertension* 46: 1135-39), and stroke (Osmond et al. (2008) *Clin Sci* 114: 37-47).

Members of the class of mineralocorticoid receptor or aldosterone antagonists that are currently marketed for clinical use include spironolactone and eplerenone.

Spironolactone is a synthetic, steroidal antimineralocorticoid agent with additional antiandrogen and weak progestogen properties, as well as some indirect estrogen and glucocorticoid effects. Spironolactone is actually a prodrug that produces canrenone as an active first metabolite. The latter is not marketed for clinical use. A number of marketed dihydropyridine calcium channel blockers have also been noted to have mineralocorticoid receptor antagonist activity (Dietz et al. (2008) *Hypertension* 51742-748). Spironolactone is used primarily as a diuretic and antihypertensive, but also for the purpose of reducing elevated or unwanted androgen activity in the body. It acts predominantly as a competitive antagonist of the mineralocorticoid receptor and belongs to a class of pharmaceutical drugs known as potassium-sparing diuretics. Spironolactone has been mostly superseded for use to treat cardiovascular conditions (e.g., heart failure and hypertension) by newer agents such as the structurally related compound eplerenone, which is also an aldosterone antagonist. Spironolactone still finds use as an antiandrogen.

Eplerenone is an aldosterone antagonist used as an adjunct in the management of chronic heart failure. It is similar to the diuretic spironolactone, though it is more selective for the mineralocorticoid receptor and thus has reduced or no antiandrogen, progestogen, or estrogenic effects. Eplerenone is specifically marketed for reducing cardiovascular risk in patients following myocardial infarction. Eplerenone is a potassium-sparing diuretic, meaning that it helps the body get rid of water but still keep potassium.

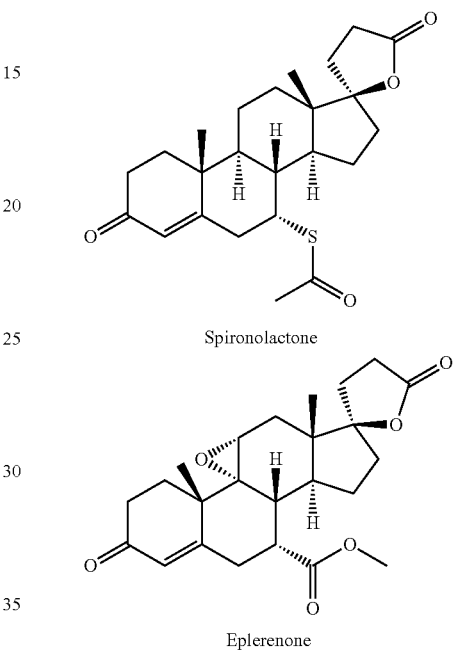

Spironolactone

Eplerenone

Other antimineralocorticoid agents include prorenone and mexrenone.

Histone Deacetylase Inhibitors

In some embodiments the drug is a histone deacetylase inhibitor. Histone deacetylase inhibitors (HDAC inhibitors, HDI) are compounds that interfere with the function of histone deacetylase. Histone deacetylases (HDAC) are a class of enzymes that remove acetyl groups (O=C—CH$_3$) from an ε-N-acetyl lysine amino acid on a histone, allowing the histones to wrap DNA more tightly. Its action is opposite to that of histone acetyltransferase (HAT), which adds acetyl groups to histones. Changes in the acetylation and de-acetylation of histones affects the wrapping of DNA around histones and these changes are involved with certain aspects of regulating gene expression. HDAC proteins are now also called lysine deacetylases (KDAC), to describe their function rather than their target, which also includes non-histone proteins.

While it is not necessary to understand the mechanism of action to practice the technology, many modes of action are known or predicted for these agents. Histone acetylation and deacetylation play important roles in the modulation of chromatin topology and the regulation of gene transcription. As such, some modes of action involve putative epigenetic pathways related to chromatin structure and the modification of nucleic acids. Histone deacetylase inhibition induces the accumulation of hyperacetylated nucleosome core histones in regions of chromatin but affects the expression of only a small subset of genes, leading to transcriptional activation of some genes, but repression of an equal or larger number of other genes. Non-histone proteins such as transcription factors are also targets for acetylation with varying functional effects. Some HDAC inhibitors have effects on non-histone proteins that are related to acetylation. HDIs can alter the degree of acetylation of these molecules and, therefore, increase or repress their activity. HDIs have been shown to alter the activity of many transcription factors, including ACTR, cMyb, E2F1, EKLF, FEN 1, GATA, HNF-4, HSP90, Ku70, NFκB, PCNA, p53, RB, Runx, SF1 Sp3, STAT, TFIIE, TCF, YY1.

Histone deacetylase inhibitors (HDIs) have found use as mood stabilizers and anti-epileptics, e.g., the drug valproic acid. Recently, HDIs have been developed for treatment of neurodegenerative disease and for cancer therapy. For example, the histone deacetylase inhibitor suberoylanilide hydroxamic acid (SAHA) find use for treatment of cutaneous T cell lymphoma (CTCL). While valproic acid has been known as an anticonvulsant for over 100 years, current studies are assessing its use on latent pools of HIV in infected persons. In addition, HDIs are currently being investigated as chemosensitizers for cytotoxic chemotherapy or radiation therapy, or in association with DNA methylation inhibitors based on in vitro synergy.

Some histone deacetylase inhibitors are cytostatic agents that inhibit the proliferation of tumor cells in vitro and in vivo by inducing cell cycle arrest, differentiation, and/or apoptosis. Acetylation enhances the activity of some transcription factors such as the tumor suppressor p53 and the erythroid differentiation factor GATA-1 but may repress transcriptional activity of others including T cell factor and the co-activator ACTR. Some studies have shown that the estrogen receptor alpha (ERalpha) is hyperacetylated in response to histone deacetylase inhibition, suppressing ligand sensitivity and regulating transcriptional activation by histone deacetylase inhibitors. Conservation of the acetylated ER-alpha motif in other nuclear receptors suggests that acetylation may play an important regulatory role in diverse nuclear receptor signaling functions.

Several well-known general broad classes of compounds are known histone deacetylase inhibitors: hydroxamic acids or hydroxamates such as trichostatin A; cyclic tetrapeptides such as trapoxin B and the depsipeptides; benzamides; electrophilic ketones; and aliphatic acid compounds such as phenylbutyrate and valproic acid. Widely used examples of the hydroxamic acids include vorinostat (SAHA), belinostat (PXD101), LAQ824, and panobinostat (LBH589); widely used examples of the benzamides include entinostat (MS-275), CI994, and mocetinostat (MGCD0103).

A number of structurally diverse histone deacetylase inhibitors have shown potent antitumor efficacy with little toxicity in vivo in animal models. Several compounds are currently in clinical development as potential treatments for solid and hematological cancers both as monotherapy and in combination with cytotoxics and differentiation agents.

Exemplary histone deacetylase inhibitors in various stages of clinical trials include, but are not limited to, vorinostat and romidepsin (for the treatment of cutaneous T cell lymphoma), panobinostat (for various cancers including cutaneous T cell lymphoma), valproic acid (for cervical cancer, ovarian cancer, and spinal muscular atrophy), belinostat (for relapsed ovarian cancer and T cell lymphoma), mocetinostat (for various cancers including follicular lymphoma, Hodgkin lymphoma, and acute myeloid leukemia), abexinostat (for sarcoma and lymphoma), etinostat (for Hodgkin lymphoma, lung cancer, and breast cancer), SB939 (for recurrent or metastatic prostate cancer), resminostat (an oral pan-HDAC inhibitor for Hodgkin lymphoma and hepatocellular carcinoma), givinostat (for refractory leukemias and myelomas), quisinostat, CUDC-101 (for cancer), AR-42 (various cancers such as relapsed or treatment-resistant multiple myeloma, chronic lymphocytic leukemia, or lymphoma), CHR-2845, CHR-3996, 4SC-202 (for advanced hematological indications), CG200745 (for solid tumors), ACY-1215 (for multiple myeloma, ME-344 (for solid refractory tumors), sulforaphane, kevetrin, trichostatin A (TSA) (for anti-inflammatory therapy), givinostat (for polycythemia vera, essential thrombocythemia, and myelofibrosis, and other agents for protecting heart muscle in acute myocardial infarction.

Suberoylanilide hydroxamic acid (SAHA) is a member of this general class of compounds that inhibits histone deacetylases (HDAC). SAHA binds to the active site of histone deacetylases and chelates zinc ions at the active site. The inhibition of histone deacetylases by SAHA results in the accumulation of acetylated histones and acetylated proteins, including transcription factors crucial for the expression of genes needed to induce cell differentiation.

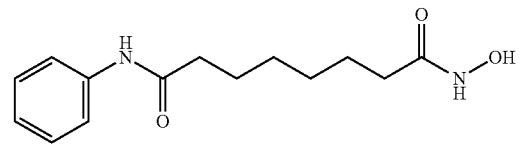

suberoylanilide hydroxamic acid (SAHA)

Chemotherapeutic Agents

Chemotherapeutic agents are typically cytotoxic antineoplastic drugs that find use as part of a standardized regimen of cancer treatment. Chemotherapy may be given with a curative intent or it may aim to prolong life or to palliate symptoms. It is often used in conjunction with other cancer treatments, such as radiation therapy or surgery. Certain chemotherapeutic agents also have a role in the treatment of other conditions, including ankylosing spondylitis, multiple sclerosis, Crohn's disease, psoriasis, psoriatic arthritis, rheumatoid arthritis, and scleroderma.

Traditional chemotherapy agents used to treat cancer act by killing cells that divide rapidly, a property of most cancer cells. Some newer anticancer drugs (for example, various monoclonal antibodies) are not indiscriminately cytotoxic, but rather target proteins that are abnormally expressed in cancer cells and that are essential for their growth. Such treatments are often referred to as targeted therapy (as distinct from classic chemotherapy) and are often used alongside traditional chemotherapeutic agents in antineoplastic treatment regimens.

Most chemotherapeutic drugs that affect cell division or DNA synthesis and function are alkylating agents, antimetabolites, anthracyclines, plant alkaloids, or topoisomerase inhibitors. Some newer agents do not directly interfere with DNA. These include monoclonal antibodies and tyrosine kinase inhibitors, which directly target a molecular abnormality in certain types of cancer (e.g., chronic myelogenous leukemia, gastrointestinal stromal tumors). These are examples of targeted therapies. In addition, some drugs that modulate tumor cell behavior without directly attacking those cells may be used. Hormone treatments fall into this category.

For example, methotrexate (MTX, formerly known as amethopterin) is an antimetabolite and antifolate drug. It is used in treatment of cancer, autoimmune diseases, ectopic pregnancy, and for the induction of medical abortions. It acts by inhibiting the metabolism of folic acid. Methotrexate was originally developed and continues to be used for chemotherapy either alone or in combination with other agents. It is effective for the treatment of a number of cancers including breast, head and neck, leukemia, lymphoma, lung, osteosarcoma, bladder, and trophoblastic neoplasms. Low doses are also used as a treatment for some autoimmune diseases, including rheumatoid arthritis, Juvenile dermatomyositis, psoriasis, psoriatic arthritis, lupus, and Crohn's disease.

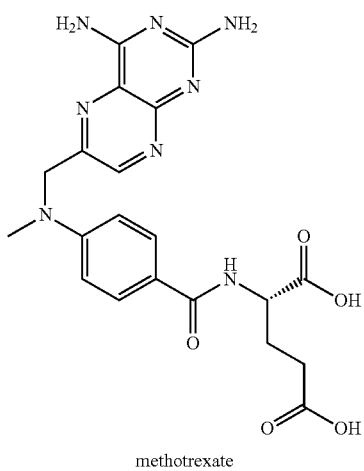 [SMILES: CN(Cc1cnc2nc(N)nc(N)c2n1)c1ccc(C(=O)N[C@@H](CCC(=O)O)C(=O)O)cc1]

methotrexate

Histone Demethylase Inhibitors

In some embodiments the drug is a histone demethylase inhibitor. Histone demethylase inhibitors are compounds that interfere with the function of histone demethylases, e.g., the product of human gene JMJD3, a JmjC family histone demethylase. JMJD3 (and other similar enzymes) removes methyl groups from lysine groups on histones. Methylation of histones is associated with transcriptional repression and is involved in some aspects of lineage determination. In particular, JMJD3 demethylates methylated (e.g., trimethylated and dimethylated) histones and plays a central role in regulating posterior development, e.g., by regulating HOX gene expression.

Moreover, JMJD3 is involved in inflammatory responses, e.g., by participating in macrophage differentiation and by regulating gene expression associated with inflammation. As such, compounds according to the technology provided herein find use as agents to modulate the inflammation response (e.g., as anti-inflammatories).

The JMJD3 gene product interacts with TLE1 and is a component of the MLL4 complex, which also comprises MLL4, ASH2L, RBBPS, WDR5, and KDM6B.

JMJD3 demethylases are found to have potential oncogenic functions; for example, JMJD3 is amplified in prostate cancer.

In some embodiments, the histone demethylase inhibitor is a compound having the structure (e.g., 3-((6-(4,5-dihydro-1H-benzo[d]azepin-3(2H)-yl)-2-(pyridin-3-yl)pyrimidin-4-yl)amino)propanoic acid):

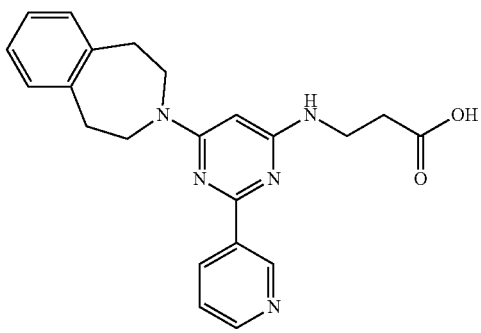 [SMILES: O=C(O)CCNc1cc(N2CCc3ccccc3CC2)nc(-c2cccnc2)n1]

Other Bioactive Agents

In some embodiments, the drug is a bioactive agent such as a therapeutic antibody and may be in some embodiments, e.g., a chimeric antibody, a humanized antibody, or a human antibody. For example, the agent may be an antibody to destroy malignant tumor cells and prevent tumor growth by blocking specific cell receptors. The antibody may be an antibody (e.g., infliximab, adalimumab) to treat an autoimmune disease such as rheumatoid arthritis, Crohn's disease, and ulcerative Colitis. In some embodiments, the antibody comprises a basiliximab or daclizumab moiety to inhibit IL-2 on activated T cells, thereby finding use in compounds to prevent rejection of transplants. In some embodiments, the antibody comprises an omalizumab moiety to inhibit human immunoglobulin E (IgE) and thus finds use in compounds to treat allergic asthma. In some embodiments, the moiety comprises ipilimumab, which blocks CTLA-4 and thus finds use in compounds for treating cancers such as melanoma. In some embodiments, the moiety comprises trastuzumab, which binds to HER2 and thus finds use in compounds for treating cancers such as breast cancers (see, e.g., Krauss et al (2000) "Emerging antibody-based HER2 (ErbB-2/neu) therapeutics", *Breast Dis* 11: 113-124).

See, e.g., Waldmann (2003) "Immunotherapy past, present and future", *Nature Medicine* 9: 269-277, for lists of exemplary FDA-approved antibodies that find use in some embodiments of the present technology, e.g., as antibodies, fragments, and/or derivatives thereof. The technology is not limited to extant therapeutic antibodies (e.g., as represented by any currently available list) but is adaptable to provide a compound comprising any therapeutic antibody known or yet to be developed.

2. Linker Groups

In some embodiments, compounds according to the technology comprise a linker group. The linker moiety provides a chemical link between the drug component and a targeting moiety and/or a detectable moiety as described in the relevant sections herein. In some embodiments the linker moiety is cleavable by an enzyme e.g., an esterase present in the target cell (e.g., an activated macrophage cell). In some embodiments, the linker moiety is cleavable by one type of esterase (e.g., a first type of an esterase present in a first cell type, e.g., a kidney cell) and is not cleavable by another type of esterase (e.g., a second type of esterase present in a second cell type, e.g., a cardiac cell). Thus, cleavage of the linker and activation of the drug and detectable moieties are specific for the targeted cell types. In some embodiments, the capability of an esterase to cleave the linker is determined by the environment (e.g., chemical or physical environment) of the esterase. For example, in some embodiments, the linker is cleavable by an esterase when the esterase is present in one type of cell, tissue, or organ, (e.g., in a kidney cell) but the linker is not cleavable when the same type of esterase is present in another type of cell, tissue, or organ (e.g., in a cardiac cell). That is, the esterase in some embodiments is susceptible to chemical and physical cues of its environment that influence its activity. In some embodiments, the linker itself is differentially cleavable in a first cell type (or tissue or organ) relative to a second cell type (or tissue or organ) based on differences in the chemical reactivity (or accessibility, etc.) of the linker moiety in the different chemical and physical environments of the first cell type relative to the second cell type.

In some embodiments, the linker moiety comprises an ester group, for example, that is cleavable by an esterase. In some embodiments the linker comprises peptide that is specifically recognized by a particular type or class of protease, e.g., matrix metalloproteinases such as matrix metalloproteinases-2 (MMP-2) and matrix metalloproteinase-9 (MMP-9), caspases, and cathepsins. For example, MMP-2 cleaves gelatin type I and collagen types IV, V, VII, X, in particular at the collagen-like sequence Pro-Gln-Gly-Ile-Ala-Gly-Gln between the Gly and Ile amino acids. MMP-9 cleaves gelatin types I and V and collagen types IV and V at particular peptide sequences in those proteins. Caspase 3 cleaves polypeptides after the tetrapeptide sequence Asp-Xaa-Xaa-Asp, with especially preferred sites having an hydrophobic amino acid residue at the second position and an hydrophilic amino acid residue at the third position (although Val or Ala are also accepted at the third position). Cathepsin B preferentially cleaves small molecule substrates after the twin arginines of an Arg-Arg-Xaa motif.

Other proteases and the peptides specifically cleaved by them are known in the art and can be found, e.g., at the TOPFind and Proteolysis Map (PMAP) databases. See, e.g., Lange et al. (2012) "TopFIND 2.0—linking protein termini with proteolytic processing and modifications altering protein function" *Nucleic Acids Res.* 40 (D1), D351-D361; Igarashi Y et al. 2009 "PMAP: databases for analyzing proteolytic events and pathways" *Nucleic Acids Res.* 37: D611-D618.

3. Cell-Targeting Moieties

In some embodiments, compounds according to the technology comprise a cell-targeting moiety. The cell targeting moiety imbues the compounds with characteristics such that the compounds are preferably recognized, bound, imported, processed, activated, etc. by one or more target cell types relative to one or more other non-target cell types. For example, endothelial cells have a high affinity for the peptide targeting moiety Arg-Gly-Asp (RGD), cancer and kidney cells preferentially interact with compounds having a folic acid moiety, immune cells have an affinity for mannose, and cardiomyocytes have an affinity for the peptide CWLSEAGPVVTVRALRGTGSW (SEQ ID NO: 2) (see, e.g., *Biomaterials* 31: 8081-8087, 2010). Other targeting moieties are known in the art. Accordingly, compounds comprising a targeting moiety preferentially interact with and are taken up by the targeted cell type.

In some embodiments, the compounds comprise an RGD peptide. RGD peptides comprise 4 to 30 (e.g., 5 to 20 or 5 to 15) amino acids. Such peptides and agents derived therefrom are known in the art, and are described by Beer et al. in *Methods Mol. Biol.* 680: 183-200 (2011) and in *Theranostics* 1: 48-57 (2011); by Morrison et al. in *Theranostics* 1: 149-153 (2011); by Zhou et al. in *Theranostics* 1: 58-82 (2011); and by Auzzas et al. in *Curr. Med. Chem.* 17: 1255-1299 (2010).

In some embodiments, the targeting moiety is folic acid, e.g., for targeting to cells expressing the folate receptor. The folate receptor is overexpressed on the cell surfaces of human cancer cells in, e.g., cancers of the brain, kidney, lung, ovary, and breast relative to lower levels in normal cells (see, e.g., Sudimack J, et al. 2000 "Targeted drug delivery via the folate receptor" *Adv Drug Deliv Rev* 41: 147-162).

In some embodiments, the targeting moiety comprises transferrin, which targets the compounds to, e.g., macrophages, erythroid precursors in bone marrow, and cancer cells. When a transferrin protein encounters a transferrin receptor on the surface of a cell, the transferrin receptor binds to the transferrin and transports the transferrin into the cell. Drugs and other compounds and/or moieties linked to the tranferrin are also transported to the cell and, in some cases, imported into the cells. In some embodiments, a fragment of a transferrin targets the compounds of the technology to the target cell. See, e.g., Qian et al. (2002) "Targeted drug delivery via the transferrin receptor-mediated endocytosis pathway", *Pharmacol. Rev.* 54: 561-87; Daniels et al. (2006) "The transferrin receptor part I: Biology and targeting with cytotoxic antibodies for the treatment of cancer", *Gun. Immunol.* 121: 144-58.

In some embodiments, the targeting moiety comprises the peptide VHSPNKK (SEQ ID NO: 6). This peptide targets compounds to cells expressing vascular cell adhesion molecule 1 (VCAM-1), e.g., to activated endothelial cells. Targeting activated endothelial cells finds use, e.g., in delivery of therapeutic agents to cells for treatment of inflammation and cancer. Certain melanoma cells use VCAM-1 to adhere to the endothelium and VCAM-1 participates in monocyte recruitment to atherosclerotic sites. Accordingly, the peptide VHSPNKK (SEQ ID NO: 6) finds use in targeting compounds of the present technology to cancer (e.g., melanoma) cells and atherosclerotic sites.

Targeting Moieties Comprising Antibodies

In some embodiments, the cell-targeting moiety comprises an antibody, or derivative or fragment thereof. Antibodies to cell-specific molecules such as, e.g., proteins (e.g., cell-surface proteins, membrane proteins, proteoglycans, glycoproteins, peptides, and the like); polynucleotides (nucleic acids, nucleotides); lipids (e.g., phospholipids, glycolipids, and the like), or fragments thereof comprising an epitope or antigen specifically recognized by the antibody, target compounds according to the technology to the cells expressing the cell-specific molecules.

For example, many antibodies and antibody fragments specifically bind markers produced by or associated with tumors or infectious lesions, including viral, bacterial, fungal, and parasitic infections, and antigens and products associated with such microorganisms (see, e.g., U.S. Pat. Nos. 3,927,193; 4,331,647; 4,348,376; 4,361,544; 4,468, 457; 4,444,744; 4,460,459; 4,460,561; 4,818,709; and 4,624,846, incorporated herein by reference) Moreover, antibodies that target myocardial infarctions are disclosed in, e.g., U.S. Pat. No. 4,036,945. Antibodies that target normal tissues or organs are disclosed in, e.g., U.S. Pat. No. 4,735,210. Anti-fibrin antibodies are known in the art, as are antibodies that bind to atherosclerotic plaque and to lymphocyte autoreactive clones.

For cancer (e.g., breast cancer) and its metastases, a specific marker or markers may be chosen from cell surface markers such as, for example, members of the MUC-type mucin family, an epithelial growth factor (EGFR) receptor, a carcinoembryonic antigen (CEA), a human carcinoma antigen, a vascular endothelial growth factor (VEGF) antigen, a melanoma antigen (MAGE) gene, family antigen, a T/Tn antigen, a hormone receptor, growth factor receptors, a cluster designation/differentiation (CD) antigen, a tumor suppressor gene, a cell cycle regulator, an oncogene, an oncogene receptor, a proliferation marker, an adhesion molecule, a proteinase involved in degradation of extracellular matrix, a malignant transformation related factor, an apoptosis related factor, a human carcinoma antigen, glycoprotein antigens, DF3, 4F2, MGFM antigens, breast tumor antigen CA 15-3, calponin, cathepsin, CD 31 antigen, proliferating cell nuclear antigen 10 (PC 10), and pS2. For other forms of cancer and their metastases, a specific marker or markers may be selected from cell surface markers such as, for example, vascular endothelial growth factor receptor (VEGFR) family, a member of carcinoembryonic antigen (CEA) family, a type of anti-idiotypic mAB, a type of ganglioside mimic, a member of cluster designation differentiation antigens, a member of epidermal growth factor receptor (EGFR) family, a type of a cellular adhesion molecule, a member of MUC-type mucin family, a type of cancer antigen (CA), a type of a matrix metalloproteinase, a type of glycoprotein antigen, a type of melanoma associated antigen (MAA), a proteolytic enzyme, a calmodulin, a member of tumor necrosis factor (TNF) receptor family, a type of angiogenesis marker, a melanoma antigen recognized by T cells (MART) antigen, a member of melanoma antigen encoding gene (MAGE) family, a prostate membrane specific antigen (PMSA), a small cell lung carcinoma antigen (SCLCA), a T/Tn antigen, a hormone receptor, a tumor suppressor gene antigen, a cell cycle regulator antigen, an oncogene antigen, an oncogene receptor antigen, a proliferation marker, a proteinase involved in degradation of extracellular matrix, a malignant transformation related factor, an apoptosis-related factor, and a type of human carcinoma antigen.

The antibody may have an affinity for a target associated with a disease of the immune system such as, for example, a protein, a cytokine, a chemokine, an infectious organism, and the like. In another embodiment, the antibody may be targeted to a predetermined target associated with a pathogen-borne condition. The particular target and the antibody may be specific to, but not limited to, the type of the pathogen-borne condition. A pathogen is defined as any disease-producing agent such as, for example, a bacterium, a virus, a microorganism, a fungus, and a parasite. The antibody may have an affinity for the pathogen or pathogen associated matter. The antibody may have an affinity for a cell marker or markers associated with a pathogen-borne condition. The marker or markers may be selected such that they represent a viable target on infected cells. For a pathogen-borne condition, the antibody may be selected to target the pathogen itself. For a bacterial condition, a predetermined target may be the bacterium itself, for example, *Escherichia coli* or *Bacillus anthracis*. For a viral condition, a predetermined target may be the virus itself, for example, Cytomegalovirus (CMV), Epstein-Barr virus (EBV), a hepatitis virus, such as Hepatitis B virus, human immunodeficiency virus, such as HIV, HIV-1, or HIV-2, or a herpes virus, such as Herpes virus 6. For a parasitic condition, a predetermined target may be the parasite itself, for example, *Trypanasoma cruzi*, Kinetoplastid, *Schistosoma mansoni*, *Schistosoma japonicum*, or *Schistosoma brucei*. For a fungal condition, a predetermined target may be the fungus itself, for example, *Aspergillus, Cryptococcus neoformans*, or *Rhizomucor*.

In another embodiment, the antibody may be targeted to a predetermined target associated with an undesirable target. The particular target and antibody may be specific to, but not limited to, the type of the undesirable target. An undesirable target is a target that may be associated with a disease or an undesirable condition, but also present in the normal condition. For example, the target may be present at elevated concentrations or otherwise be altered in the disease or undesirable state. Antibody may have an affinity for the undesirable target or for biological molecular pathways related to the undesirable target. Antibody may have an affinity for a cell marker or markers associated with the undesirable target. For an undesirable target, the choice of a predetermined target may be important to therapy utilizing the compounds according to the present technology (e.g., the drug and/or therapeutic moieties). The antibody may be selected to target biological matter associated with a disease or undesirable condition. For arteriosclerosis, a predetermined target may be, for example, apolipoprotein B on low density lipoprotein (LDL). For obesity, a predetermined marker or markers may be chosen from cell surface markers such as, for example, one of gastric inhibitory polypeptide receptor and CD36 antigen. Another undesirable predetermined target may be clotted blood. In another embodiment, the antibody may be targeted to a predetermined target associated with a reaction to an organ transplanted into the patient. The particular target and antibody may be specific to, but not limited to, the type of organ transplant. The antibody may have an affinity for a biological molecule associated with a reaction to an organ transplant. The antibody may have an affinity for a cell marker or markers associated with a reaction to an organ transplant. The marker or markers may be selected such that they represent a viable target on T cells or B cells of the immune system. In another embodiment, the antibody may be targeted to a predetermined target associated with a toxin in the patient. A toxin is defined as any poison produced by an organism including, but not limited to, bacterial toxins, plant toxins, insect toxin, animal toxins, and man-made toxins. The particular target and antibody may be specific to, but not limited to, the type of toxin. The antibody may have an affinity for the toxin or a biological molecule associated with a reaction to the toxin. The antibody may have an affinity for a cell marker or markers associated with a reaction to the toxin. In another embodiment, the antibody may be targeted to a predetermined target associated with a hormone-related disease. The particular target and antibody may be specific to, but not limited to, a particular hormone disease. The antibody may have an affinity for a hormone or a biological molecule associated with the hormone pathway. The antibody may have an affinity for a cell marker or markers associated with the hormone disease. In another embodiment, the antibody may be targeted to a predetermined target associated with non-cancerous diseased tissue. The particular target and antibody may be specific to, but not limited to, a particular non-cancerous diseased tissue, such as non-cancerous diseased deposits and precursor deposits. The antibody may have an affinity for a biological molecule associated with the non-cancerous diseased tissue. The antibody may have an affinity for a cell marker or markers associated with the non-cancerous diseased tissue. In another embodiment, the antibody may be targeted to a proteinaceous pathogen. The particular target and antibody may be specific to, but not limited to, a particular proteinaceous pathogen. The antibody may have an affinity for a proteinaceous pathogen or a biological molecule associated with the proteinaceous pathogen. The antibody may have an affinity for a cell marker or markers associated with the proteinaceous pathogen. For prion diseases, also known as transmissible spongiform encephalopathies, a predetermined target may be, for example, Prion protein 3F4.

See, e.g., U.S. Pat. Appl. Pub. No. 20050090732, incorporated herein by reference (in particular Table I) for a list of targets, cell-specific markers (e.g., antigens for targeting with an antibody moiety), antibodies, and indications associated with those targets, cell-specific markers, and antigens/antibodies.

4. Detectable Moieties

In some embodiments, compounds according to the technology comprise a detectable moiety. In some embodiments, the detectable moiety is not detectable while chemically linked to the drug component and is detectable when not chemically linked to the drug component. For example, in some embodiments the detectable moiety is not detectable while linked to the drug component and becomes detectable after the linker moiety is cleaved and the detectable moiety is freed from the compound. As such, both the drug component and the detectable moiety are in an inactive state until the linker is cleaved (e.g., in a target cell by an esterase). Detecting the detectable moiety thus provides an indicator of the presence of active drug in the target cells.

In some embodiments, the detectable moiety is a fluorogenic dye. Several classes of fluorogenic dyes and specific compounds are known that are appropriate for particular embodiments of the technology: xanthene derivatives such as fluorescein, rhodamine, Oregon green, eosin, and Texas red; cyanine derivatives such as cyanine, indocarbocyanine, oxacarbocyanine, thiacarbocyanine, and merocyanine; naphthalene derivatives (dansyl and prodan derivatives); coumarin derivatives; oxadiazole derivatives such as pyridyloxazole, nitrobenzoxadiazole, and benzoxadiazole; pyrene derivatives such as cascade blue; oxazine derivatives such as Nile red, Nile blue, cresyl violet, and oxazine 170; acridine derivatives such as proflavin, acridine orange, and acridine yellow; arylmethine derivatives such as auramine, crystal violet, and malachite green; and tetrapyrrole derivatives such as porphin, phtalocyanine, bilirubin.

In some embodiments, the detectable moiety is an imaging agent such as is used for positron emission tomography (PET) (e.g., $^{18}$F-fluorodeoxyglucose). In some embodiments, the detectable moiety is a contrast agent such as is used in magnetic resonance imaging (MRI). One exemplary agent is the heavy metal imaging agent DOTA-Gd, which is the chelating agent DOTA (1,4,7,10-tetraazacyclododecane-1,4,7,10-tetraacetic acid) complexed with the lanthanide element gadolinium (Gd). Other contrast agents comprise iron oxide, iron platinum particles, and manganese.

These moieties can be incorporated into the compounds using specific functional groups, active ester, carboxylate, isothiocyanate, and hydrazine for reaction with amino groups, carbodiimides for reaction with carboxyl groups, maleimide and acetyl bromide for reaction with thiols.

Detection of the detectable moiety is accomplished by any suitable, appropriate means (e.g., fluorimetry for a fluorescent dye, PET, MRI, radiometry, etc.)

5. Other Functional Groups

In some embodiments, the compounds comprise other functional groups. For example, in some embodiments the compounds comprise dendrimers, magnetic beads, polymer (e.g., polystyrene beads). These groups have properties conferring particular advantages to the compounds. For example, dendrimers provide a functional group for conjugating other chemical species to the dendrimer surface that can function as detecting agents (such as a dye molecule), affinity ligands, targeting components, radioligands, imaging agents, or pharmaceutically active compounds. Magnetic beads find use in isolation of compounds and/or in tracing compounds.

Pharmaceutical Formulations

It is generally contemplated that the compounds related to the technology are formulated for administration to a mammal, and especially to a human with a condition that is responsive to the administration of such compounds. Therefore, where contemplated compounds are administered in a pharmacological composition, it is contemplated that the contemplated compounds are formulated in admixture with a pharmaceutically acceptable carrier. For example, contemplated compounds can be administered orally as pharmacologically acceptable salts, or intravenously in a physiological saline solution (e.g., buffered to a pH of about 7.2 to 7.5). Conventional buffers such as phosphates, bicarbonates, or citrates can be used for this purpose. Of course, one of ordinary skill in the art may modify the formulations within the teachings of the specification to provide numerous formulations for a particular route of administration. In particular, contemplated compounds may be modified to render them more soluble in water or other vehicle, which for example, may be easily accomplished with minor modifications (salt formulation, esterification, etc.) that are well within the ordinary skill in the art. It is also well within the ordinary skill of the art to modify the route of administration and dosage regimen of a particular compound to manage the pharmacokinetics of the present compounds for maximum beneficial effect in a patient.

In certain pharmaceutical dosage forms, prodrug forms of contemplated compounds may be formed for various purposes, including reduction of toxicity, increasing the organ or target cell specificity, etc. Among various prodrug forms, acylated (acetylated or other) derivatives, pyridine esters, and various salt forms of the present compounds are preferred. One of ordinary skill in the art will recognize how to readily modify the present compounds to prodrug forms to facilitate delivery of active compounds to a target site within the host organism or patient. One of ordinary skill in the art will also take advantage of favorable pharmacokinetic parameters of the prodrug forms, where applicable, in delivering the present compounds to a targeted site within the host organism or patient to maximize the intended effect of the compound. Similarly, it should be appreciated that contemplated compounds may also be metabolized to their biologically active form, and all metabolites of the compounds herein are therefore specifically contemplated. In addition, contemplated compounds (and combinations thereof) may be administered in combination with yet further agents.

With respect to administration to a subject, it is contemplated that the compounds be administered in a pharmaceutically effective amount. One of ordinary skill recognizes that a pharmaceutically effective amount varies depending on the therapeutic agent used, the subject's age, condition, and sex, and on the extent of the disease in the subject. Generally, the dosage should not be so large as to cause adverse side effects, such as hyperviscosity syndromes, pulmonary edema, congestive heart failure, and the like. The dosage can also be adjusted by the individual physician or veterinarian to achieve the desired therapeutic goal.

As used herein, the actual amount encompassed by the term "pharmaceutically effective amount" will depend on the route of administration, the type of subject being treated, and the physical characteristics of the specific subject under consideration. These factors and their relationship to determining this amount are well known to skilled practitioners in the medical, veterinary, and other related arts. This amount and the method of administration can be tailored to maximize efficacy but will depend on such factors as weight, diet, concurrent medication, and other factors that those skilled in the art will recognize.

Pharmaceutical compositions preferably comprise one or more compounds of the present technology associated with one or more pharmaceutically acceptable carriers, diluents, or excipients. Pharmaceutically acceptable carriers are known in the art such as those described in, for example, *Remingtons Pharmaceutical Sciences*, Mack Publishing Co. (A. R. Gennaro edit. 1985), explicitly incorporated herein by reference for all purposes.

Accordingly, in some embodiments, the immunotherapeutic agent is formulated as a tablet, a capsule, a time release tablet, a time release capsule; a time release pellet; a slow release tablet, a slow release capsule; a slow release pellet; a fast release tablet, a fast release capsule; a fast release pellet; a sublingual tablet; a gel capsule; a microencapsulation; a transdermal delivery formulation; a transdermal gel; a transdermal patch; a sterile solution; a sterile solution prepared for use as an intramuscular or subcutaneous injection, for use as a direct injection into a targeted site, or for intravenous administration; a solution prepared for rectal administration; a solution prepared for administration through a gastric feeding tube or duodenal feeding tube; a suppository for rectal administration; a liquid for oral consumption prepared as a solution or an elixir; a topical cream; a gel; a lotion; a tincture; a syrup; an emulsion; or a suspension.

In some embodiments, the time release formulation is a sustained-release, sustained-action, extended-release, controlled-release, modified release, or continuous-release mechanism, e.g., the composition is formulated to dissolve quickly, slowly, or at any appropriate rate of release of the compound over time.

In some embodiments, the compositions are formulated so that the active ingredient is embedded in a matrix of an insoluble substance (e.g., various acrylics, chitin) such that the dissolving compound finds its way out through the holes in the matrix, e.g., by diffusion. In some embodiments, the formulation is enclosed in a polymer-based tablet with a laser-drilled hole on one side and a porous membrane on the other side. Stomach acids push through the porous membrane, thereby pushing the drug out through the laser-drilled hole. In time, the entire drug dose releases into the system while the polymer container remains intact, to be excreted later through normal digestion. In some sustained-release formulations, the compound dissolves into the matrix and the matrix physically swells to form a gel, allowing the compound to exit through the gel's outer surface. In some embodiments, the formulations are in a micro-encapsulated form, e.g., which is used in some embodiments to produce a complex dissolution profile. For example, by coating the compound around an inert core and layering it with insoluble substances to form a microsphere, some embodiments provide more consistent and replicable dissolution rates in a convenient format that is combined in particular embodiments with other controlled (e.g., instant) release pharmaceutical ingredients, e.g., to provide a multipart gel capsule.

In some embodiments, the pharmaceutical preparations and/or formulations of the technology are provided in particles. "Particles" as used herein means nano- or microparticles (or in some instances larger) that can consist in whole or in part of the compounds as described herein. The particles may contain the preparations and/or formulations in a core surrounded by a coating, including, but not limited to, an enteric coating. The preparations and/or formulations also may be dispersed throughout the particles. The preparations and/or formulations also may be adsorbed into the particles. The particles may be of any order release kinetics, including zero order release, first order release, second order release, delayed release, sustained release, immediate release, and any combination thereof, etc. The particle may include, in addition to the preparations and/or formulations, any of those materials routinely used in the art of pharmacy and medicine, including, but not limited to, erodible, non-erodible, biodegradable, or nonbiodegradable materials or combinations thereof. The particles may be microcapsules which contain the formulation in a solution or in a semi-solid state. The particles may be of virtually any shape.

Both non-biodegradable and biodegradable polymeric materials can be used in the manufacture of particles for delivering the preparations and/or formulations. Such polymers may be natural or synthetic polymers. The polymer is selected based on the period of time over which release is desired. Bioadhesive polymers of particular interest include bioerodible hydrogels described by H. S. Sawhney, C. P. Pathak and J. A. Hubell in *Macromolecules*, (1993) 26: 581-587, the teachings of which are incorporated herein by reference. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly (isobutyl methacrylate), poly(hexylmethacrylate), poly(isodecyl methacrylate), poly(lauryl methacrylate), poly(phenylmethacrylate), poly(methyl acrylate), poly(isopropyl acrylate), poly(isobutyl acrylate), and poly(octadecyl acrylate).

The technology also provides methods for preparing stable pharmaceutical preparations containing aqueous solutions of the compounds or salts thereof to inhibit formation of degradation products. A solution is provided that contains the compound or salts thereof and at least one inhibiting agent. The solution is processed under at least one sterilization technique prior to and/or after terminal filling the solution in the sealable container to form a stable pharmaceutical preparation. The present formulations may be prepared by various methods known in the art so long as the formulation is substantially homogenous, e.g., the pharmaceutical is distributed substantially uniformly within the formulation. Such uniform distribution facilitates control over drug release from the formulation.

In some embodiments, the compound is formulated with a buffering agent. The buffering agent may be any pharmaceutically acceptable buffering agent. Buffer systems include citrate buffers, acetate buffers, borate buffers, and phosphate buffers. Examples of buffers include citric acid, sodium citrate, sodium acetate, acetic acid, sodium phosphate and phosphoric acid, sodium ascorbate, tartartic acid, maleic acid, glycine, sodium lactate, lactic acid, ascorbic acid, imidazole, sodium bicarbonate and carbonic acid, sodium succinate and succinic acid, histidine, and sodium benzoate and benzoic acid.

In some embodiments, the compound is formulated with a chelating agent. The chelating agent may be any pharmaceutically acceptable chelating agent. Chelating agents include ethylenediaminetetraacetic acid (also synonymous with EDTA, edetic acid, versene acid, and sequestrene), and EDTA derivatives, such as dipotassium edetate, disodium edetate, edetate calcium disodium, sodium edetate, trisodium edetate, and potassium edetate. Other chelating agents include citric acid and derivatives thereof. Citric acid also is known as citric acid monohydrate. Derivatives of citric acid include anhydrous citric acid and trisodiumcitrate-dihydrate.

Still other chelating agents include niacinamide and derivatives thereof and sodium desoxycholate and derivatives thereof.

In some embodiments, the compound is formulated with an antioxidant. The antioxidant may be any pharmaceutically acceptable antioxidant. Antioxidants are well known to those of ordinary skill in the art and include materials such as ascorbic acid, ascorbic acid derivatives (e.g., ascorbylpalmitate, ascorbylstearate, sodium ascorbate, calcium ascorbate, etc.), butylated hydroxy anisole, buylated hydroxy toluene, alkylgallate, sodium meta-bisulfate, sodium bisulfate, sodium dithionite, sodium thioglycollic acid, sodium formaldehyde sulfoxylate, tocopherol and derivatives thereof, (d-alpha tocopherol, d-alpha tocopherol acetate, dl-alpha tocopherol acetate, d-alpha tocopherol succinate, beta tocopherol, delta tocopherol, gamma tocopherol, and d-alpha tocopherol polyoxyethylene glycol 1000 succinate) monothioglycerol, and sodium sulfite. Such materials are typically added in ranges from 0.01 to 2.0%.

In some embodiments, the compound is formulated with a cryoprotectant. The cryoprotecting agent may be any pharmaceutically acceptable cryoprotecting agent. Common cryoprotecting agents include histidine, polyethylene glycol, polyvinyl pyrrolidine, lactose, sucrose, mannitol, and polyols.

In some embodiments, the compound is formulated with an isotonicity agent. The isotonicity agent can be any pharmaceutically acceptable isotonicity agent. This term is used in the art interchangeably with iso-osmotic agent, and is known as a compound which is added to the pharmaceutical preparation to increase the osmotic pressure, e.g., in some embodiments to that of 0.9% sodium chloride solution, which is iso-osmotic with human extracellular fluids, such as plasma. Preferred isotonicity agents are sodium chloride, mannitol, sorbitol, lactose, dextrose and glycerol.

The pharmaceutical preparation may optionally comprise a preservative. Common preservatives include those selected from the group consisting of chlorobutanol, parabens, thimerosol, benzyl alcohol, and phenol. Suitable preservatives include but are not limited to: chlorobutanol (0.3-0.9% w/v), parabens (0.01-5.0%), thimerosal (0.004-0.2%), benzyl alcohol (0.5-5%), phenol (0.1-1.0%), and the like.

In some embodiments, the compound is formulated with a humectant to provide a pleasant mouth-feel in oral applications. Humectants known in the art include cholesterol, fatty acids, glycerin, lauric acid, magnesium stearate, pentaerythritol, and propylene glycol.

In some embodiments, an emulsifying agent is included in the formulations, for example, to ensure complete dissolution of all excipients, especially hydrophobic components such as benzyl alcohol. Many emulsifiers are known in the art, e.g., polysorbate 60.

For some embodiments related to oral administration, it may be desirable to add a pharmaceutically acceptable flavoring agent and/or sweetener. Compounds such as saccharin, glycerin, simple syrup, and sorbitol are useful as sweeteners.

Administration, Treatments, and Dosing

In some embodiments, the technology relates to methods of providing a dosage of a theranostic compound to a subject. The methods comprise the general steps of administering a compound according to the technology, measuring a level of a detectable label in a sample obtained from the subject, and adjusting the dose based on the measured level of the detectable label. In particular, after administration, activities (e.g., enzymes such as esterases) in the target cells process the compounds of the technology (e.g., by cleaving the linker moiety) to produce the active drug and the cleaved detectable label in a one-to-one ratio. As such, measuring the amount of free detectable label in a sample from the subject provides a measure of the amount of active drug in the target cells in the subject. Using this information, dosages are adjusted (e.g., increased, decreased, not changed) to provide the required or appropriate amount of drug at the target cells. This process may be repeated as needed to adjust the dose and thus to provide an effective treatment. Such a process provides nearly real-time monitoring and adjustment of dosages in a subject.

In some embodiments, a compound, a derivative thereof, or a pharmaceutically acceptable salt thereof, is administered in a pharmaceutically effective amount. In some embodiments, a compound, a derivative thereof, or a pharmaceutically acceptable salt thereof, is administered in a therapeutically effective dose.

The dosage amount and frequency are selected to create an effective level of the compound without substantially harmful effects. When administered orally or intravenously, the dosage of the compound or related compounds will generally range from 0.001 to 10,000 mg/kg/day or dose (e.g., 0.01 to 1000 mg/kg/day or dose; 0.1 to 100 mg/kg/day or dose).

Methods of administering a pharmaceutically effective amount include, without limitation, administration in parenteral, oral, intraperitoneal, intranasal, topical, sublingual, rectal, and vaginal forms. Parenteral routes of administration include, for example, subcutaneous, intravenous, intramuscular, intrastemal injection, and infusion routes. In some embodiments, the compound, a derivative thereof, or a pharmaceutically acceptable salt thereof, is administered orally.

In some embodiments, a single dose of a compound or a related compound is administered to a subject. In other embodiments, multiple doses are administered over two or more time points, separated by hours, days, weeks, etc. In some embodiments, compounds are administered over a long period of time (e.g., chronically), for example, for a period of months or years (e.g., 1, 2, 3, 4, 5, 6, 7, 8, 9, 10, 11, 12, or more months or years). In such embodiments, compounds may be taken on a regular scheduled basis (e.g., daily, weekly, etc.) for the duration of the extended period.

The technology also relates to methods of treating a subject with a drug appropriate for the subject's malady. According to another aspect of the technology, a method is provided for treating a subject in need of such treatment with an effective amount of a compound or a salt thereof. The method involves administering to the subject an effective amount of a compound or a salt thereof in any one of the pharmaceutical preparations described above, detailed herein, and/or set forth in the claims. The subject can be any subject in need of such treatment. In the foregoing description, the technology is in connection with a compound or salts thereof. Such salts include, but are not limited to, bromide salts, chloride salts, iodide salts, carbonate salts, and sulfate salts. It should be understood, however, that the compound is a member of a class of compounds and the technology is intended to embrace pharmaceutical preparations, methods, and kits containing related derivatives within this class. Another aspect of the technology then embraces the foregoing summary but read in each aspect as if any such derivative is substituted wherever "compound" appears.

In some embodiments, a subject is tested to assess the presence, the absence, or the level of a malady and/or a condition. Such testing is performed, e.g., by assaying or measuring a biomarker, a metabolite, a physical symptom, an indication, etc., to determine the risk of or the presence of the malady or condition. In some embodiments, the subject is treated with a compound based on the outcome of the test. In some embodiments, a subject is treated, a sample is obtained and the level of detectable agent is measured, and then the subject is treated again based on the level of detectable agent that was measured. In some embodiments, a subject is treated, a sample is obtained and the level of detectable agent is measured, the subject is treated again based on the level of detectable agent that was measured, and then another sample is obtained and the level of detectable agent is measured. In some embodiments, other tests (e.g., not based on measuring the level of detectable agent) are also used at various stages, e.g., before the initial treatment as a guide for the initial dose. In some embodiments, a subsequent treatment is adjusted based on a test result, e.g., the dosage amount, dosage schedule, identity of the drug, etc. is changed. In some embodiments, a patient is tested, treated, and then tested again to monitor the response to therapy and/or change the therapy. In some embodiments, cycles of testing and treatment may occur without limitation to the pattern of testing and treating, the periodicity, or the duration of the interval between each testing and treatment phase. As such, the technology contemplates various combinations of testing and treating without limitation, e.g., test/treat, treat/test, test/treat/test, treat/test/treat, test/treat/test/treat, test/treat/test/treat/test, test/treat/test/treat/treat/treat/test, treat/treat/test/treat, test/treat/treat/test/treat/treat, etc.

EXAMPLES

Example 1—Cell-Specific Mineralocorticoid Receptor Theranostics for Inflammatory Diseases Macrophages participate in inflammatory pathways that are central to the pathologies of many diseases, including rheumatoid arthritis, coronary artery disease, diabetes mellitus, heart failure, hypertension, Alzheimer's disease, and cancer. Mineralocorticoid receptors in the cytoplasm of macrophages are activated by a number of ligands, including glucocorticoids (e.g., cortisol) and mineralocorticoids (e.g., aldosterone). Upon activation, mineralocorticoid receptors translocate to the cell nucleus where they activate genes that are involved in producing pro-inflammatory agents that are secreted by the macrophages to further the inflammatory cascade.

Aldosterone is a circulating hormone that is a mineralocorticoid receptor agonist. Consequently, through its action on mineralocorticoid receptors, aldosterone promotes inflammation and, as a result in some cases, cardiovascular disease. Agents that block the action of aldosterone on the mineralocorticoid receptor, such as certain mineralocorticoid receptor antagonists, have been studied in patients suffering from heart failure and reduced left ventricular ejection. These therapies provide some of the few therapeutic approaches that are consistently associated with clinical benefits, including improvements in patient survival.

Aldosterone antagonists compete with aldosterone to bind to mineralocorticoid receptors. The conventional mineralocorticoid receptor antagonists spironolactone and eplerenone inhibit inflammation associated with mineralocorticoid receptor activation and are effective in inhibiting sodium reabsorption and decreasing blood pressure. However, conventional aldosterone antagonists often have off-target and/or systemic effects. For example, adverse drug reactions associated with spironolactone include electrolyte disturbances, hyperkalemia, leukopenia, thrombocytopenia, and abnormal hepatic and renal function. As a result of its structural similarity to progesterone, spironolactone produces progestogenic and anti-androgenic adverse effects such as gynecomastia, testicular atrophy, sexual dysfunction, and menstrual irregularities. Eplerenone, though more selective for the mineralocorticoid receptor relative to some other nuclear hormone receptors, has also been associated with hyperkalemia. As such, despite having some clinical benefits, conventional mineralocorticoid receptor antagonists are limited by undesirable effects and thus their clinical application is limited.

Activated macrophages that are involved in pro-inflammatory pathways express certain intracellular esterases that mediate some of their pro-inflammatory functions. In some aspects, the technology is related to the enzymatic activities of these various esterases. For example, the technology finds use in delivering therapeutic mineralocorticoid receptor antagonists specifically to activated macrophages only in the target organs, e.g., to the heart, but not to the kidney nor to other mineralocorticoid receptor responsive target organs. This delivery system also provides for the targeting of the kidney but not the heart. As such, the technology provides organ specific mineralocorticoid receptor antagonists.

Synthesis of Eplerenone-7'-Fluorescein-Alkyne During the development of embodiments of the technology provided herein, particular compounds were synthesized and synthesis schemes were developed. In some embodiments, an eplerenone "sensor" was produced. This compound finds use in indicating the presence of an active eplerenone compound in a biological system.

Methods $^1$H NMR spectra were obtained using a Varian Inova 500 MHz. Electrospray ionization mass spectra (ESI-MS) were recorded using a Micromass Quattro II Electronic HPLC/MS/MS mass spectrometer.

Materials

All solvents and chemicals were of reagent grade quality (Sigma-Aldrich, St. Louis, Mo.) and used without further purification unless otherwise noted. Thin-layer Chromatography (TLC) and column chromatography were performed with 25 DC-Plastikfolien Kieselgel 60 F254 (Merck) and Baxter silica gel 60 Å (230-400 mesh), respectively.

Discussion

The eplerenone sensor comprises two components: eplerenone and a quenched fluorescein dye. In general, the synthetic scheme first modifies fluorescein with an alkyne group (e.g., attached by a nonhydrolyzelable ether linkage) and then couples the modified fluorescein to eplereone at the 7 position (e.g., using a hydrolyzable ester linkage). See FIG. 1.

In some embodiments, particular synthetic schemes to make the eplerenone sensor comprise four steps (e.g., as shown in the scheme of FIG. 1: (1) fluorescein is alkylated with 4-bromo-1-butyne to produce alkyne-O-fluorescein (Compound 1); (2) eplerenone is treated with LiOH (aq.) to yield free carboxyl groups for further modification. Both ester bonds at the 7 and 17 positions are hydrolyzed; (3) the reaction mixture is acidified by HCl and the carboxyl group at the 17 position is converted to a lactone structure to yield eplerenone-7'-acid (Compound 2); (4) alkyne-O-fluorescein (Compound 1) is coupled with eplerenone-7'-acid (Compound 2) to produce the eplerenone sensor eplerenone-7'-fluorescein-O-alkyne (Compound 3).

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the technology as claimed should not be unduly limited to such specific embodiments. Indeed, various modifications of the described modes for carrying out the technology that are obvious to those skilled in pharmacology, biochemistry, medical science, or related fields are intended to be within the scope of the following claims.

We claim:

1. A theranostic compound comprising a structure according to

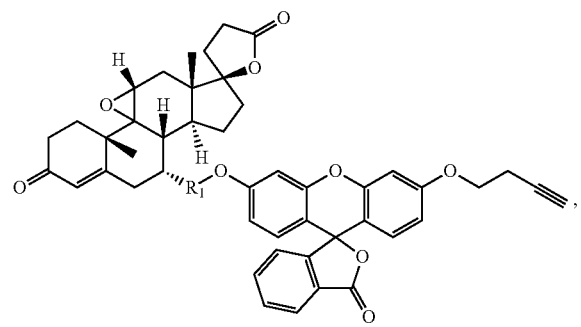

and wherein $R_1$ comprises a carbonyl or a protease-cleavable linker.

2. A method of treating a subject, the method comprising:
   1) administering to the subject a theranostic compound comprising:
      a) a bioactive component;
      b) a detectable component linked to the bioactive component by a linker; and
      c) a targeting component,
      wherein the theranostic compound has a structure according to

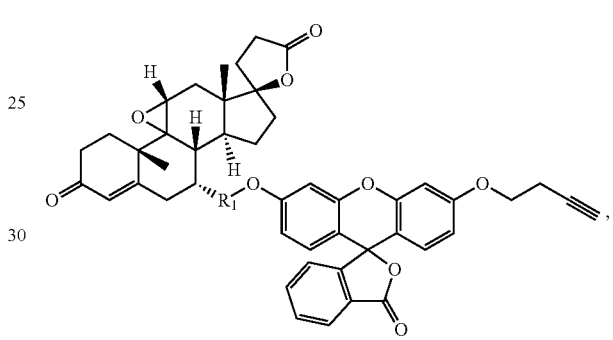

wherein said linker comprises $R_1$ and $R_1$ comprises a carbonyl or a protease-cleavable linker, and
   wherein the bioactive component is not active and the detectable component is not detectable when the detectable component is linked to the bioactive component by the enzyme-cleavable linker; and
   2) measuring a level of the detectable component in a sample from the subject.

3. The method of claim 2 further comprising a second administering of the theranostic compound to the subject according to the level of the detectable component in the sample from the subject.

4. The method of claim 2 further comprising determining an amount of the bioactive component at a target site of the subject.

5. The method of claim 2 wherein a cell-specific activity at a target site of the subject breaks the linker.

6. A method of treating a subject comprising administering to the subject the theranostic compound according to claim 1.

* * * * *

```
                            SEQUENCE LISTING

<160> NUMBER OF SEQ ID NOS: 6

<210> SEQ ID NO 1
    <211> LENGTH: 3
    <212> TYPE: PRT
    <213> ORGANISM: Artificial Sequence
    <220> FEATURE:
    <223> OTHER INFORMATION: Synthetic

<400> SEQUENCE: 1

Arg Gly Asp
    1

<210> SEQ ID NO 2
    <211> LENGTH: 21
    <212> TYPE: PRT
    <213> ORGANISM: Artificial Sequence
    <220> FEATURE:
    <223> OTHER INFORMATION: Synthetic

<400> SEQUENCE: 2

Cys Trp Leu Ser Glu Ala Gly Pro Val Val Thr Val Arg Ala Leu Arg
    1               5                   10                  15

Gly Thr Gly Ser Trp
                20

<210> SEQ ID NO 3
    <211> LENGTH: 7
    <212> TYPE: PRT
    <213> ORGANISM: Artificial Sequence
    <220> FEATURE:
    <223> OTHER INFORMATION: Synthetic

<400> SEQUENCE: 3

Pro Gln Gly Ile Ala Gly Gln
    1               5

<210> SEQ ID NO 4
    <211> LENGTH: 4
    <212> TYPE: PRT
    <213> ORGANISM: Artificial Sequence
    <220> FEATURE:
    <223> OTHER INFORMATION: Synthetic
    <220> FEATURE:
    <221> NAME/KEY: misc_feature
    <222> LOCATION: (2)..(3)
    <223> OTHER INFORMATION: Xaa can be any naturally occurring amino acid

<400> SEQUENCE: 4

Asp Xaa Xaa Asp
    1

<210> SEQ ID NO 5
    <211> LENGTH: 3
    <212> TYPE: PRT
    <213> ORGANISM: Artificial Sequence
    <220> FEATURE:
    <223> OTHER INFORMATION: Synthetic
    <220> FEATURE:
    <221> NAME/KEY: misc_feature
```

```
<222> LOCATION: (3)..(3)
<223> OTHER INFORMATION: Xaa can be any naturally occurring amino acid

<400> SEQUENCE: 5

Arg Arg Xaa
1

<210> SEQ ID NO 6
<211> LENGTH: 7
<212> TYPE: PRT
<213> ORGANISM: Artificial Sequence
<220> FEATURE:
<223> OTHER INFORMATION: Synthetic

<400> SEQUENCE: 6

Val His Ser Pro Asn Lys Lys
1               5
```